United States Patent
Kast et al.

(10) Patent No.: US 9,517,352 B2
(45) Date of Patent: Dec. 13, 2016

(54) ACCESSORY APPARATUS FOR IMPROVED RECHARGING OF IMPLANTABLE MEDICAL DEVICE

(75) Inventors: John E. Kast, Hugo, MN (US); Steve T. Deininger, Blaine, MN (US); Raymond F. McMullen, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1667 days.

(21) Appl. No.: 12/725,603

(22) Filed: Mar. 17, 2010

(65) Prior Publication Data
US 2010/0241194 A1    Sep. 23, 2010

Related U.S. Application Data

(60) Provisional application No. 61/161,908, filed on Mar. 20, 2009.

(51) Int. Cl.
| A61N 1/37 | (2006.01) |
|---|---|
| A61N 1/375 | (2006.01) |
| A61N 1/378 | (2006.01) |
| A61N 1/372 | (2006.01) |

(52) U.S. Cl.
CPC .............. *A61N 1/375* (2013.01); *A61N 1/3787* (2013.01); *A61N 1/37229* (2013.01)

(58) Field of Classification Search
USPC ..................................................... 607/36–37
See application file for complete search history.

(56) References Cited

U.S. PATENT DOCUMENTS

| 3,357,437 A | 12/1967 | Abell |
| 3,598,128 A * | 8/1971 | Chardack ..................... 607/27 |
| 3,888,260 A | 6/1975 | Fischell |
| 4,041,955 A | 8/1977 | Kelly et al. |
| 4,071,032 A | 1/1978 | Schulman |
| 4,134,408 A | 1/1979 | Brownlee et al. |

(Continued)

FOREIGN PATENT DOCUMENTS

| EP | 0499939 A1 | 2/1992 |
| EP | 0499939 B1 | 2/1992 |

(Continued)

OTHER PUBLICATIONS

Medtronic, Inc., "Implantable Neurostimulation Systems", 1998.
(Continued)

*Primary Examiner* — Amanda Patton
(74) *Attorney, Agent, or Firm* — Beth L. McMahon

(57) ABSTRACT

An apparatus configured to be placed about an implantable medical device having a face with a geometric center offset from a center of a recharge coil of the device includes first and second opposing major exterior surfaces, and a continuous exterior side surface joining the first and second opposing major exterior surfaces. A cavity is defined between, and an opening is formed by, the first and second major surfaces and the continuous side surface. The opening is in communication with the cavity and is configured to allow the device to access the cavity. An asymmetric region, adjacent to the cavity, is formed between a portion of the first and second major surfaces and the continuous side surface. The asymmetric region is configured to shift the geometric center of the combined apparatus and device, when the device is received in the cavity, towards the center of the recharge coil.

19 Claims, 7 Drawing Sheets

(56) References Cited

U.S. PATENT DOCUMENTS

| | | |
|---|---|---|
| 4,186,749 A | 2/1980 | Fryer |
| 5,279,292 A | 1/1994 | Baumann et al. |
| 5,314,457 A | 5/1994 | Jeutter et al. |
| 5,411,537 A | 5/1995 | Munshi et al. |
| 5,527,348 A | 6/1996 | Winkler et al. |
| 5,562,714 A | 10/1996 | Grevious |
| 5,613,935 A | 3/1997 | Jarvik |
| 5,690,693 A | 11/1997 | Wang et al. |
| 5,713,939 A | 2/1998 | Nedungadi et al. |
| 5,733,313 A | 3/1998 | Barreras, Sr. et al. |
| 5,861,019 A | 1/1999 | Sun et al. |
| 6,067,474 A | 5/2000 | Schulman et al. |
| 6,154,677 A | 11/2000 | Leysieffer |
| 6,178,353 B1 | 1/2001 | Griffith et al. |
| 6,275,737 B1 | 8/2001 | Mann |
| 6,308,101 B1 | 10/2001 | Faltys et al. |
| 6,324,430 B1 | 11/2001 | Zarinetchi et al. |
| 6,505,077 B1 | 1/2003 | Kast et al. |
| 6,516,227 B1 | 2/2003 | Meadows et al. |
| 7,454,251 B2 * | 11/2008 | Rezai et al. ................ 607/115 |
| 7,596,408 B2 * | 9/2009 | Singhal et al. ................ 607/3 |
| 2009/0018600 A1 * | 1/2009 | Deininger et al. ............ 607/36 |

FOREIGN PATENT DOCUMENTS

| | | |
|---|---|---|
| EP | 0811395 A2 | 12/1997 |
| EP | 1048324 A2 | 11/2000 |
| WO | 98/37926 | 9/1998 |
| WO | 99/06108 | 2/1999 |
| WO | 99/44684 | 9/1999 |
| WO | 00/01442 | 1/2000 |
| WO | 01/83029 A1 | 11/2001 |
| WO | 01/97908 A2 | 12/2001 |
| WO | 01/97908 A3 | 12/2001 |

OTHER PUBLICATIONS

Sinha, Gunjan, "The Heart, Medicine & Health", Popular Science, p. 43, Feb. 2000.

Medtronic, Inc., "Mattrix Neurostimulation System", Brochure, 1995.

* cited by examiner

ACCESSORY APPARATUS FOR IMPROVED RECHARGING OF IMPLANTABLE MEDICAL DEVICE

CROSS-REFERENCE TO RELATED APPLICATIONS

The present application claims priority to U.S. Provisional Patent Application No. 61/161,908, filed Mar. 20, 2009, the entire disclosure of which is incorporated herein by reference.

FIELD

This application relates to implantable medical devices, more particularly rechargeable devices and apparatuses for improving recharging and apparatuses managing implanted leads.

BACKGROUND

Implantable medical devices are used to treat a variety of diseases, and their use is increasing. Many implantable medical devices employ medical leads to deliver electrical therapy to a patient or to monitory patient parameters. The leads are connected to the active device, which is typically implanted subcutaneously in the patient, and extend from the implanted device to a target location of the patient. The leads typically have a length greater than needed to extend from the device to the target location to ensure that the lead will be of sufficient length for almost all patients and almost all circumstances. Typically the lead is tunneled from the subcutaneous pocket to the target location. Excess lead length is then wrapped or coiled and placed in the subcutaneous pocket. The manner in which the lead is wrapped or coiled can vary from implanting surgeon to implanting surgeon and can affect, among other things, flex life performance of the lead, the extent of lead abrasion, and the size of the implant pocket and corresponding incision.

Problems with lead abrasion may be exacerbated with rechargeable active implantable medical devices and excess coiled lead. If the coiled excess lead or a portion of the lead crosses the face of the device between the device and the patient's skin, the likelihood of lead abrasion may increase. Because the primary recharge coil of an external recharge head is placed adjacent the patient's skin in a location over the implanted device, the lead may be impacted between the recharge head and the implanted device causing abrasion of the lead.

In many rechargeable implantable devices, the secondary coil or the recharge coil of the implantable device is not centered on the geometric center of the device, which could lead to inefficient recharge. When the patient recharges the implantable device, the patient palpates their skin to identify the location of the implanted device. The recharge head is then located over the skin in the location identified by the patient. If the patient centers the recharge head the geometric center of the implanted device and the geometric center of the recharge device is not the center of the recharge device, coupling between the primary and secondary coils may not be optimized and thus may be inefficient.

BRIEF SUMMARY

Among other things, apparatuses for aligning a secondary recharge coil of an implantable medical device with the geometric center of a face of the device are described herein. Such apparatuses should improve recharge efficiency of the implantable medical device. The alignment apparatuses may include lead management features for managing excess lead length in proximity to an implanted medical device. Such apparatuses may improve flex life performance, reduce lead abrasion, or may decrease the size of the implant pocket. In some embodiments, the apparatuses described herein include one or more elutable therapeutic agents for treating a disease or complication associated with implantation of the device. For example, an apparatus may include an anti-inflammatory agent or local anesthetic for mitigating pain associated with implant, or may include an anti-infective agent to treat or prevent infection that may occur following implantation.

In various embodiments, a system includes a rechargeable implantable medical device. The device has an exterior face having a geometric center. The device includes a recharge coil where the center of the recharge coil is offset from the geometric center of the face. The system further includes an apparatus configured to be disposed about at least a portion of the device such that the device and apparatus together define a combined face with a geometric center substantially aligned with the center of the recharge coil.

In various embodiments, an apparatus configured to be placed about an implantable medical device having a face with a geometric center offset from a center of a recharge coil of the device includes first and second opposing major exterior surfaces, and a continuous exterior side surface joining the first and second opposing major exterior surfaces. A cavity is defined between the first and second major surfaces and the continuous side surfaces. The cavity is configured to receive the implantable medical device. An opening in the apparatus is formed by the first and second major surfaces and the continuous side surface. The opening is in communication with the cavity and is configured to allow at least a portion of the device to access the cavity. An asymmetric region is formed between a portion of the first and second major surfaces and the continuous side surface. The asymmetric region is adjacent to the cavity and is configured to shift the geometric center of the combined apparatus and device, when the device is received in the cavity, towards the center of the recharge coil of the device.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "aligned" with regard to a an apparatus configured to "align" the geometric center of a combined apparatus and device with the center of a recharge coil, means that the combined center is 70% or more (e.g., 80% or more, 90% or more, or 95% or more) closer to the center of the recharge coil than the geometric center of the device alone.

This disclosure relates to apparatuses for aligning a secondary recharge coil of an implantable medical device with the geometric center of a face of the device. By aligning the effective center of the device with the center of the recharge coil, better or more efficient recharge should be attainable. Such alignment apparatuses may include lead management features, which may improve flex life performance, reduce lead abrasion, or may decrease the size of the implant pocket.

Figure 1:
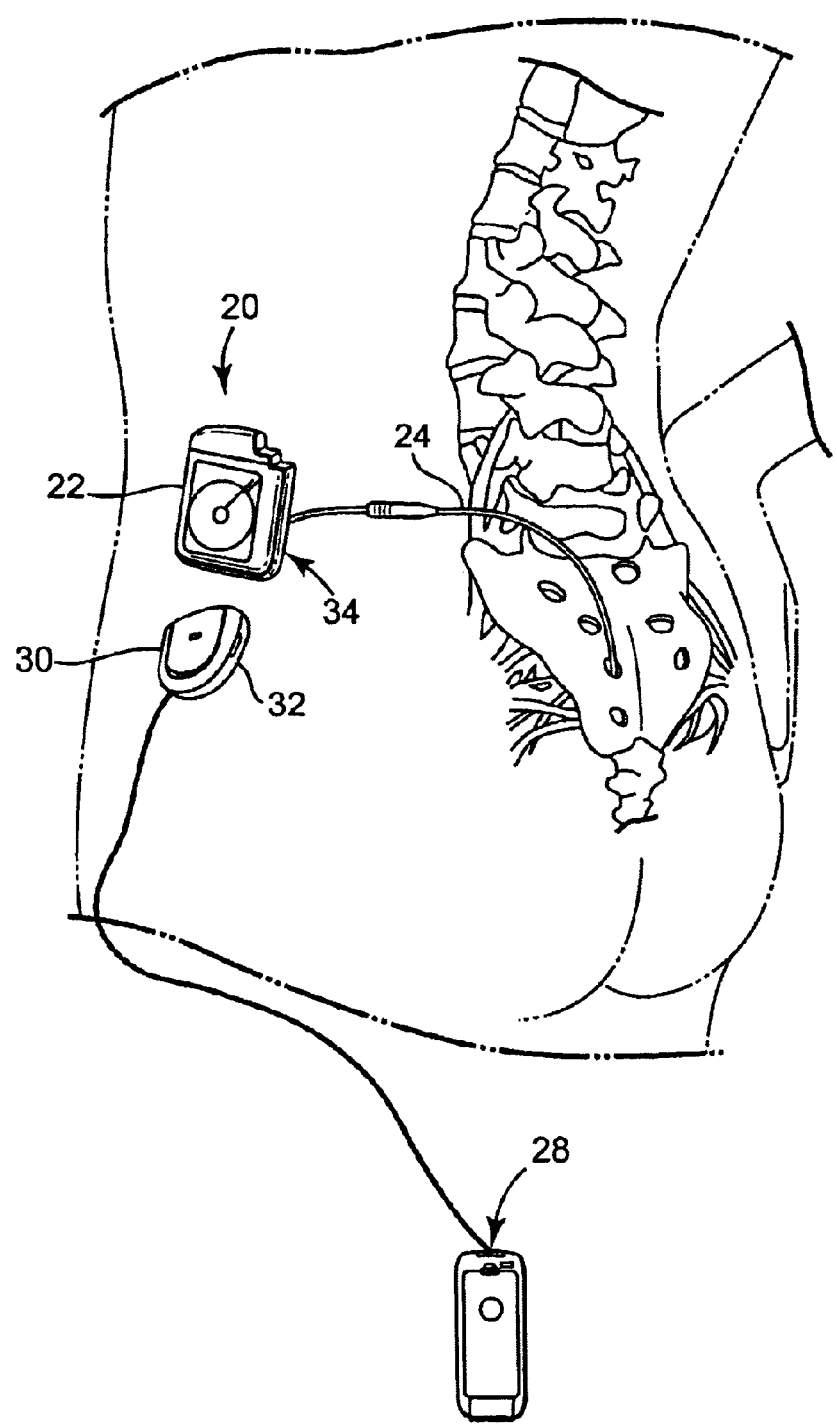
FIG. 1 is a schematic illustration showing a recharge environment of an implantable medical device.

Referring to FIG. 1, a general environment of a rechargeable implantable medical device 20 is shown. An implantable neurostimulator 22 is shown in FIG. 1, but other embodiments such as pacemakers, defibrillators, diagnostic recorders, cochlear implants, drug infusion devices and the like are also applicable. Implantable medical devices 20 are often implanted subcutaneously about a centimeter below the surface of the skin with an electrical lead 24 extending to one or more therapy sites. The rechargeable implantable medical device 20 is recharged with a recharging device 28 such as a patient charger or programmer that also has a charging capability.

Recharging an implantable medical device 20 generally begins with placing a recharging head 30 containing a primary recharging coil 32 against the patient's skin near the proximal side of the medical device 20. A patient or healthcare provider may palpate the patient's skin to determine the location of the implanted device 20 for proper placement and alignment of the recharge head 30. Some rechargers 28 have an antenna locator that indicates when the recharge head 30 is aligned closely enough with the implanted medical device 20 for adequate inductive charge coupling. The recharge power transfer signal is typically a frequency that will penetrate transcutaneously to the location of the implanted medical device 20, such as a frequency in the range from 5.0 KHz to 120 KHz. The power transfer signal may be converted by the implantable medical device 20 into regulated DC power that is used to charge a rechargeable power source 34.

For rechargers 28 not having an antenna locator, it may be difficult for a patient to properly align the recharge head with the implanted medical device 20, particularly if the center of the recharge coil of the implanted device 20 is not centered with the geometric center of the proximal face of the device 20.

Figure 2:
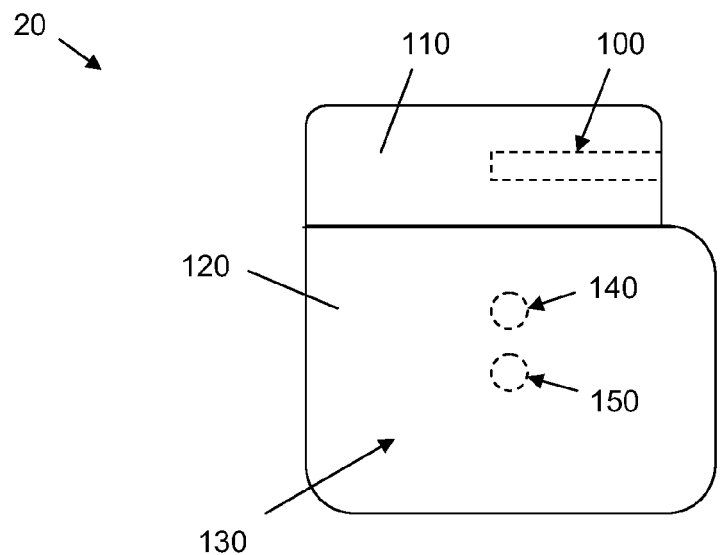
FIG. 2 is a schematic side view of an implantable medical device.

For example, and with reference to FIG. 2, a schematic side view of an implantable medical device 20 is shown. The device 20 includes a receptacle 100 for receiving a lead and electrically coupling the lead to electronics disposed in the device 20. The receptacle 100 in the depicted embodiment is formed in a header 110. The header 110 is mounted on a hermetically sealed housing 120 of the device 20. Hermetically sealed feedthroughs electrically couple internal contacts of the receptacle 100 to the electronics contained within housing 120. The internal contacts of the receptacle 100 are positioned and configured to electrically couple to contacts of a lead inserted into the receptacle 100.

The device 20 has a proximal exterior face 130 having a geometric center 140. The proximal face 130 is configured to be implanted adjacent a patient's skin such that a recharge head may be placed in proximity to the face 130 to recharge the device, which contains a recharge coil (not shown). The center of the recharge coil 150 is offset from the geometric center of the face 140.

Figure 3A:
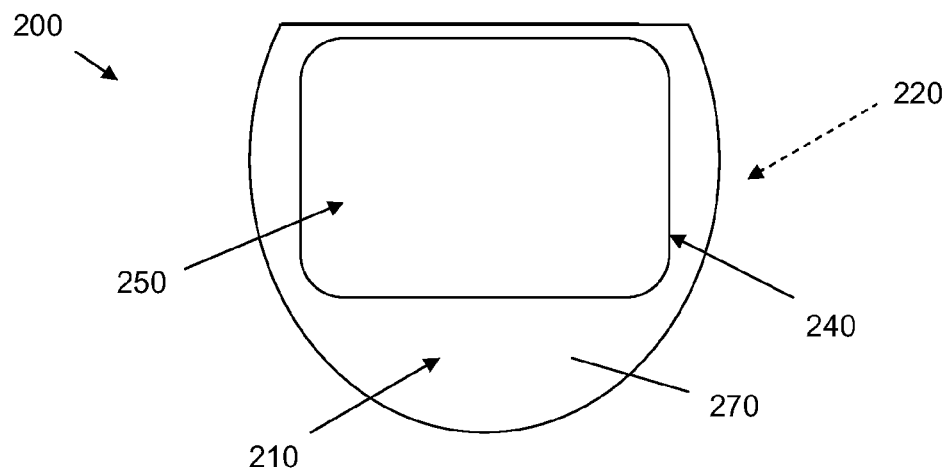
FIG. 3A is a schematic side view of an apparatus configured to be placed about an implantable medical device.
Figure 3B:
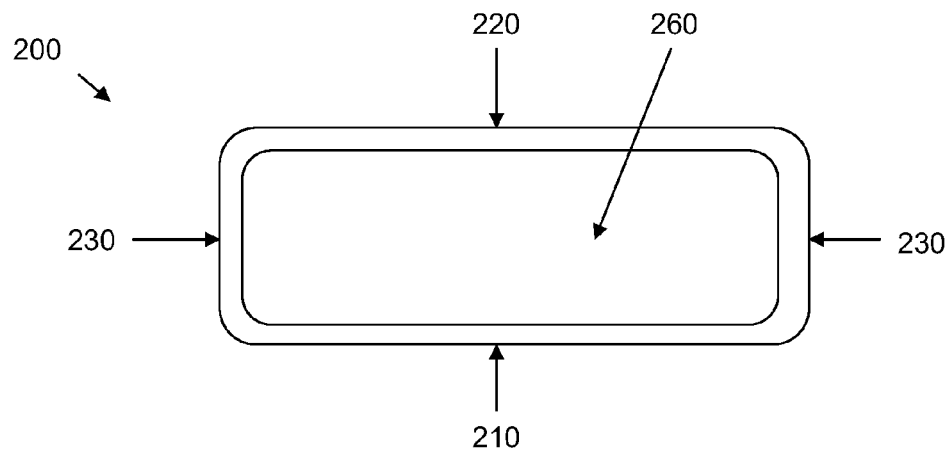
FIG. 3B is a top-down view of an exemplary embodiment of an apparatus shown in FIG. 3A.
Figure 3C:
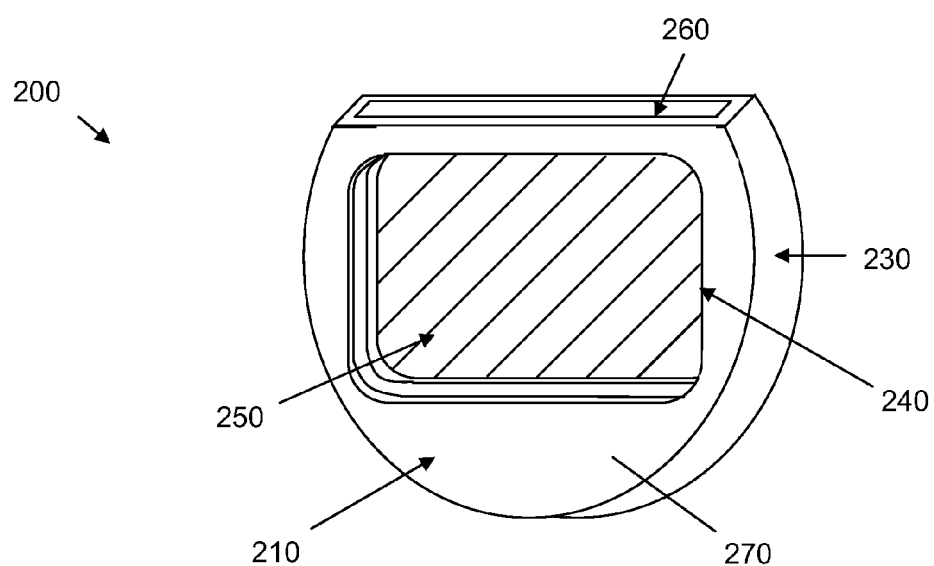
FIG. 3C is a schematic perspective view of an exemplary embodiment of the apparatus shown in FIG. 3A.

Referring now to FIGS. 3A-C, a schematic side view is shown of an apparatus 200 configured to be placed about an implantable medical device having a face with a geometric center offset from a center of a recharge coil of the device. The apparatus has first 210 and second 220 opposing major exterior surfaces and a continuous exterior side surface 230 joining the first 210 and second 220 exterior major surfaces. An opening 240 may be formed in the first major surface 210 to allow the face of the implantable medical device to be exposed when the apparatus 200 is disposed about the device. A cavity 250 is formed between the first 210 and second 220 major surfaces and the continuous side surface 230. The cavity 250 is configured to receive the implantable medical device. A top opening 260 is formed by the first 210 and second 220 major surfaces and the continuous side surface 230. The top opening 260 is in communication with the cavity 250 and is configured to allow at least a portion of the device to access the cavity 250. An asymmetric portion 270 is formed between a portion of the first 210 and second 220 major surfaces and the continuous side surface 230. The asymmetric portion 270 is adjacent to the cavity 250 and is configured to shift the geometric center of the combined apparatus and device, when the device is received in the cavity, towards the center of the recharge coil of the device.

Figure 4:
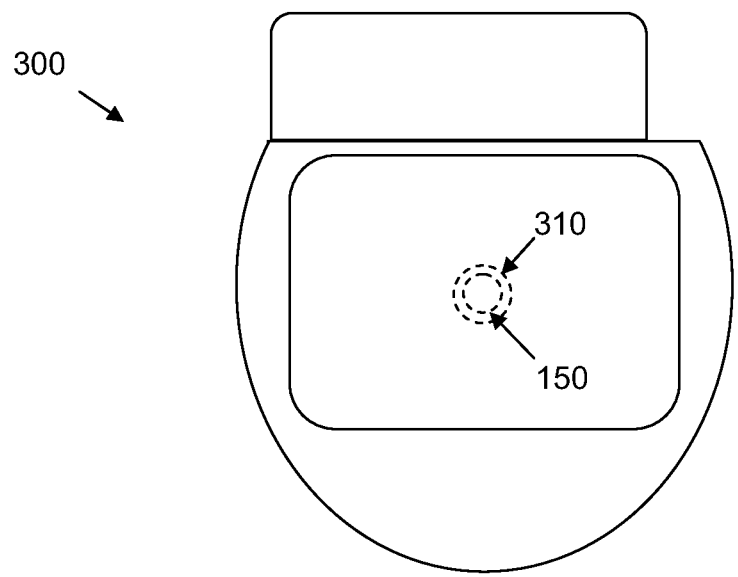
FIG. 4 is a schematic side view of the apparatus of FIG. 3 placed about the device of FIG. 2.

For example and with reference to FIG. 4, a schematic side view of a device received by a cavity of an apparatus is shown. The geometric center 310 of the combined device and apparatus 300 is aligned with the center 150 of the recharge coil of the device. Accordingly, when the patient in which the combined device and apparatus 300 is implanted palpates their skin to identify the location of the device for recharging, the center of the combined device will correspond to the center of the recharge coil, allowing the patient to more efficiently recharge the device.

Figure 5:
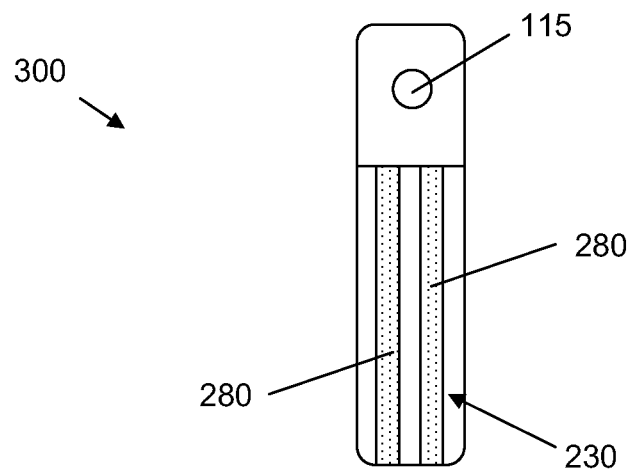
FIG. 5 is schematic front view of the apparatus and device in FIG. 4.
Figure 6:
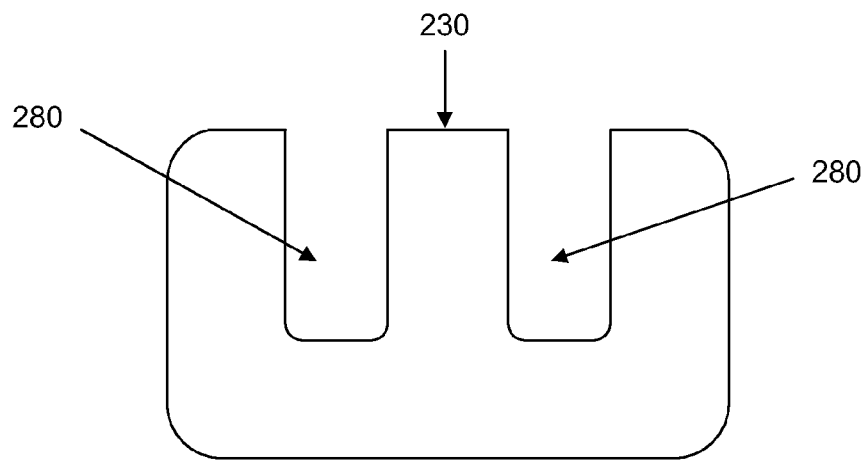
FIG. 6 is a schematic cross section of the apparatus depicted in FIGS. 3-5.

Referring now to FIG. 5, the apparatus shown in the depicted embodiment includes grooves 280 formed in the continuous side surface 230. The grooves 280 are configured to receive and retain a lead that exits the opening 115 of a lead receptacle of the implantable medical device about which the apparatus is placed. The groves 280 run circumferentially around the proximal recharge face of the device to prevent the lead from lying across the face of the device to minimize lead abrasion due to being crushed between the recharge face of the device and a recharge head. FIG. 6 shows a sectional view of grooves 280 formed in the side surface 230. Multiple grooves 280 allow for the lead to be wrapped around the device multiple times in a managed and reliable manner.

Figure 7:
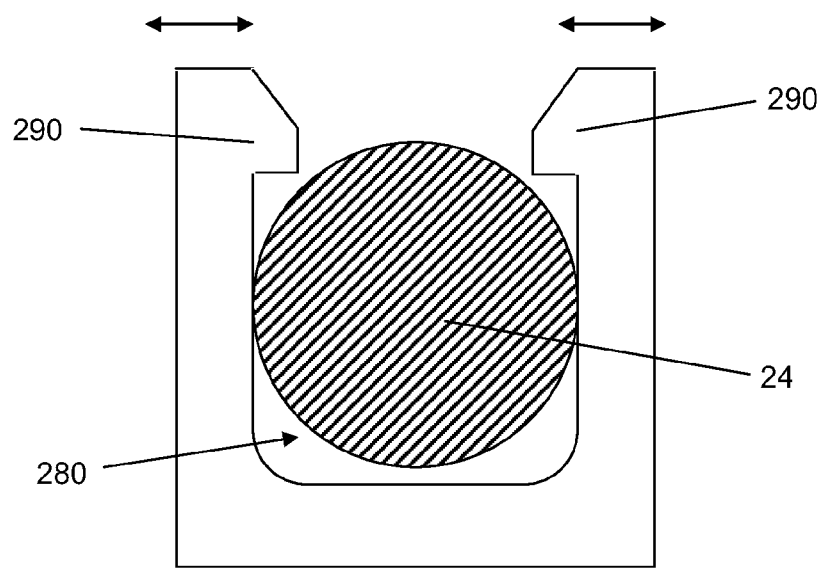
FIG. 7 is a schematic cross section of an alternative exemplary embodiment of the apparatus depicted in FIGS. 3-5 with a lead being retained by the apparatus.
Figure 8:
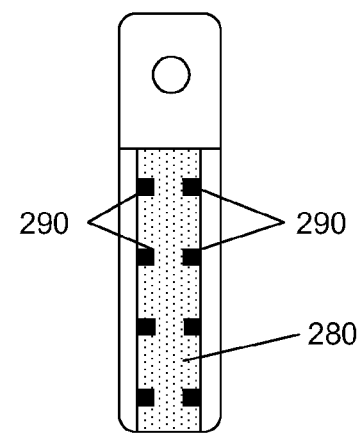
FIG. 8 is a schematic front view of an apparatus as shown in FIG. 7 disposed about a device as shown in FIG. 2.

With reference to FIGS. 7-8, opposing tabs 290 may form a portion of a groove 280. The tabs 290 are configured to separate from a relaxed position to allow a lead 24 to access the groove and to resiliently return to the relaxed position to retain the lead 24 within the groove 280. As shown in FIG. 8, a series of opposed tabs 290 may be included along the length of a groove 280 to facilitate retaining a lead that exits an opening 115 of a receptacle of the device.

Figure 9:
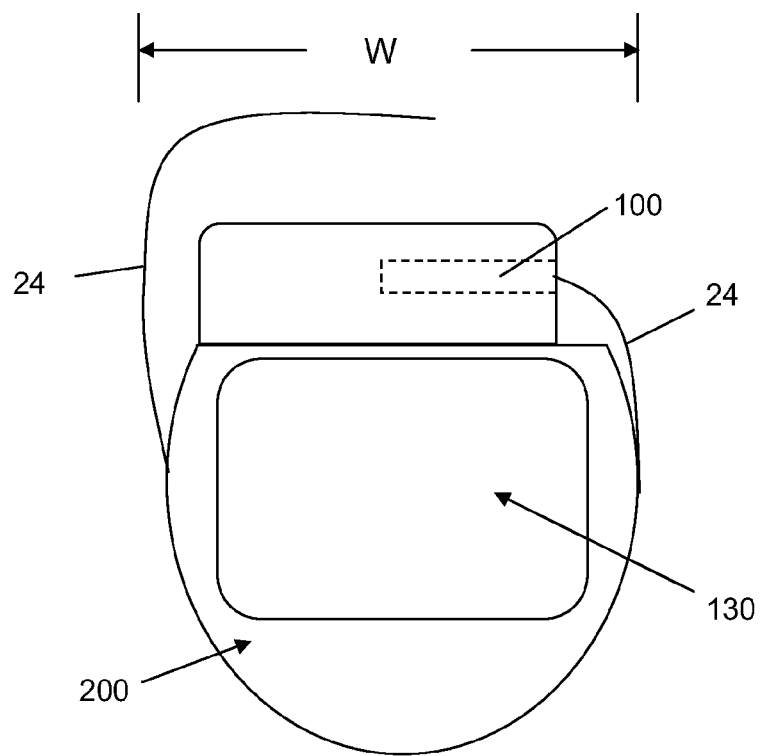
FIG. 9 is a schematic side view of a device and lead with a lead management apparatus as shown in FIG. 3.
Figure 10:
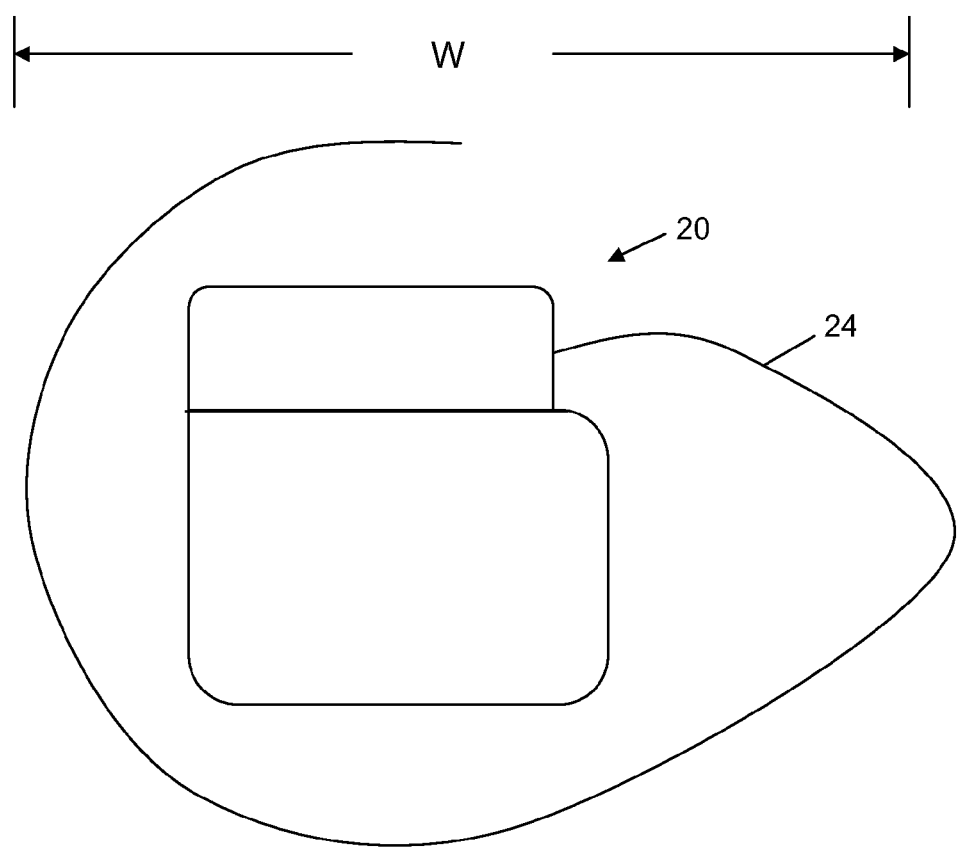
FIG. 10 is schematic side view of a device and lead without a lead management apparatus.

As shown in FIG. 9, the grooves retain the lead 24 exiting the receptacle 100 of the device to provide excess lead maintenance. As discussed above, the circumferential grooves keep the lead 240 from lying across the proximal recharge face 130 of a rechargeable device. The lead maintenance aspect of the apparatus for shifting the geometric center also reduces the overall effective width W of the device (compare to the effective width W of a device 20 without a corresponding lead maintenance apparatus shown in FIG. 10). By keeping the lead 24 in close proximity to the device, the effective width W is minimized, allowing for a smaller surgical pocket and incision. Smaller surgical pockets and incisions are likely to reduce complications, such as infection, and patient discomfort. In addition, attempting to force a device having a large effective width W into a small surgical pocket may result in lead kinking and reliability issues that may be mitigated through the lead management embodiments discussed and contemplated herein.

Center shifting or lead management apparatuses as described above, or portions thereof, may be made of any suitable medical acceptable material. Examples of polymeric materials that may be employed include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE). In many embodiments, an apparatus as described herein is formed from an elastomeric polymer, such as silicone.

The apparatus may be molded or otherwise formed. The apparatus may be formed such that the portion of the apparatus grippingly engages the rechargeable device or also may be formed using an adhesive, such as medical adhesive, to bond the apparatus to the device.

In various embodiments, a therapeutic agent is incorporated into or onto at least a portion of an apparatus as described herein. Any suitable therapeutic agent may be included in the apparatus. Examples of suitable therapeutic agents are described in U.S. Pre-Grant Published Patent Application Publication No. 2006/0129221, entitled "Tunneling Guide," published on Jun. 15, 2006, which published patent application is hereby incorporated herein by reference in its entirety to the extent that it does not conflict with the disclosure presented herein. By way of example, one or more anti-inflammatory agents, local anesthetics, analgesic, or anti-infective agents may be incorporated in or on an apparatus.

In some embodiments, an anti-infective agent is incorporated in or on at least a portion of an apparatus described herein. Preferably, the anti-infective agent is present in or on the apparatus, or may be eluted from the apparatus, in an amount sufficient to prevent an infection from forming in a pocket into which the device is implanted. It is also desirable that the anti-infective agent, in the concentration present in the apparatus or portion thereof, be nontoxic when implanted in the patient. It will be understood that more than one anti-infective agent may be present in or on the apparatus. Non-limiting examples of such agents include antibiotics and antiseptics.

Any antibiotic suitable for use in a human may be used in accordance with various embodiments of the invention. An antibiotic may have bateriostatic or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. One of ordinary skill in the art will recognize other antibiotics that may be used.

It is desirable that the selected antibiotic(s) kill or inhibit the growth of one or more bacteria that are associated with infection following surgical implantation of a medical device. Such bacteria are recognized by those of ordinary skill in the art and include *Stapholcoccus aureus* and

*Staphlococcus epidermis*. Preferably, the antibiotic(s) selected are effective against strains of bacteria that are resistant to one or more antibiotic.

To enhance the likelihood that bacteria will be killed or inhibited, it may be desirable to combine one or more antibiotics. It may also be desirable to combine one or more antibiotics with one or more antiseptics. It will be recognized by one of ordinary skill in the art that antimicrobial agents having different mechanisms of action or different spectrums of action may be most effective in achieving such an effect. In a particular embodiment, a combination of rifampin and minocycline is used.

Any antiseptic suitable for use in a human may be used in accordance with various embodiments of the invention. Antiseptics are agents capable of killing or inhibiting the growth of one or more of bacteria, fungi, or viruses. Antiseptics include disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver sulfadiazine and alcohols. One of ordinary skill in the art will recognize other antiseptics.

It is desirable that the antiseptic(s) selected kill or inhibit the growth of one or more microbes that are associated with infection following surgical implantation of a medical device. Such bacteria are recognized by those of ordinary skill in the art and include *Stapholcoccus aureus, Staphlococcus epidermis, Pseudomonus auruginosa*, and *Candidia*.

To enhance the likelihood that microbes will be killed or inhibited, it may be desirable to combine one or more antiseptics. It may also be desirable to combine one or more antiseptics with one or more antibiotics. It will be recognized by one of ordinary skill in the art that antimicrobial agents having different mechanisms of action or different spectrums of action may be most effective in achieving such an effect. In a particular embodiment, a combination of chlorohexidine and silver sulfadiazine is used.

An anti-infective agent, such as an antibiotic or antiseptic, may be present in the apparatus at any concentration effective, either alone or in combination with another anti-infective agent, to prevent an infection within a pocket into which the apparatus is implanted. Generally, an antiseptic agent may be present in the apparatus at a range of between about 0.5% and about 20% by weight. For example, the anti-infective agent may be present in the apparatus or portion thereof at a range of between about 0.5% and about 15% by weight or between about 0.5% and about 10% by weight.

An anti-infective agent may be incorporated into or on a polymeric apparatus using any known or developed technique. For example, the anti-infective agent may be adhered to a surface of the apparatus, adsorbed into the apparatus, or compounded into the polymeric material that forms the apparatus. Accordingly, the anti-infective material may be embedded, coated, mixed or dispersed on or in the material of the apparatus. In various embodiments, the anti-infective agent may be incorporated into the polymeric apparatus as taught in U.S. Pat. Nos. 5,217,493 or 5,624,704.

Thus, embodiments of ACCESSORY APPARATUS FOR IMPROVED RECHARGING OF IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system comprising:
    a rechargeable implantable medical device,
    wherein the implantable medical device has an exterior face, the exterior face having a geometric center,
    wherein the implantable medical device includes a recharge coil, wherein the center of the recharge coil is offset from the geometric center of the exterior face; and
    an apparatus configured to be disposed about at least a portion of the implantable medical device such that the implantable medical device and apparatus together define a combined face with a geometric center aligned with the center of the recharge coil.

2. A system according to claim 1, wherein the apparatus comprises a groove configured to receive a lead.

3. A system according to claim 2, wherein the groove runs circumferentially around the combined face.

4. A system according to claim 2, wherein the apparatus further comprises opposing tabs defining a portion of the groove, the opposing tabs configured to separate from a relaxed position to allow the lead to access the groove and to resiliently return to the relaxed position to retain the lead in the groove.

5. A system according to claim 1, wherein the apparatus is formed from silicone.

6. A system according to claim 1, wherein the apparatus comprises one or more elutable therapeutic agents.

7. A system according to claim 6, wherein the one or more elutable therapeutic agents comprise an anti-infective agent.

8. A system according to claim 6, wherein the one or more elutable therapeutic agents comprise minocycline and rifampin.

9. An apparatus configured to be placed about an implantable medical device having a face with a geometric center offset from a center of a recharge coil of the implantable medical device, the apparatus comprising:
    first and second opposing major exterior surfaces;
    a continuous exterior side surface joining the first and second opposing major exterior surfaces;
    a cavity defined between the first and second major surfaces and the continuous side surfaces, wherein the cavity is configured to receive the implantable medical device, wherein an opening in the apparatus is formed by the first and second major surfaces and the continuous side surface, wherein the opening is in communication with the cavity and is configured to allow at least a portion of the implantable medical device to access the cavity; and
    an asymmetric region formed between a portion of the first and second major surfaces and the continuous side surface, wherein the asymmetric region is adjacent to the cavity and wherein the implantable medical device and apparatus together define a combined face and wherein the geometric center of the combined face aligns with the center of the recharge coil.

10. An apparatus according to claim 9, wherein the apparatus comprises a groove formed around the continuous exterior side surface configured to receive a lead.

11. An apparatus according to claim 10, wherein the groove runs circumferentially around the face of the implantable medical device.

12. An apparatus according to claim 10, wherein the apparatus further comprises opposing tabs defining a portion of the groove, the opposing tabs configured to separate from a relaxed position to allow the lead to access the groove and to resiliently return to the relaxed position to retain the lead in the groove.

13. An apparatus according to claim 10, wherein the apparatus is formed from silicone.

14. An apparatus according to claim 10, wherein the apparatus further comprises one or more elutable therapeutic agents.

15. An apparatus according to claim 14, wherein the one or more elutable therapeutic agents comprise an anti-infective agent.

16. An apparatus according to claim 14, wherein the one or more elutable therapeutic agents comprise minocycline and rifampin.

17. A method for aligning a recharge coil of an implantable medical device, wherein the implantable medical device has an exterior face with a geometric center and wherein the center of the recharge coil is offset from the geometric center of the exterior face of the implantable medical device, the method comprising:

placing an apparatus about the implantable medical device such that the apparatus and the implantable medical device together define a combined face with a geometric center aligned with the center of the recharge coil.

18. A method according to claim 17, wherein at least a portion of the combined face comprises the exterior face of the implantable medical device.

19. A method according to claim 17, wherein the apparatus includes a cavity, and wherein placing the apparatus about the implantable medical device comprises allowing at least a portion of the implantable medical device to access the cavity.

* * * * *